(12) United States Patent
Filliers et al.

(10) Patent No.: US 7,572,916 B2
(45) Date of Patent: Aug. 11, 2009

(54) DIASTEREOSELECTIVE SYNTHESIS PROCESS WITH 6-BROMO-4-(3-CHLOROPHENYL)-2-METHOXY-QUINOLINE

(75) Inventors: Walter Ferdinand Maria Filliers, Vremde (BE); Rudy Laurent Maria Broeckx, Turnhout (BE); Patrick René Angibaud, Fontaine-Bellenger (FR)

(73) Assignee: Janssen Pharmaceutica NV, Beerse (BE)

( * ) Notice: Subject to any disclaimer, the term of this patent is extended or adjusted under 35 U.S.C. 154(b) by 121 days.

(21) Appl. No.: 11/568,420

(22) PCT Filed: Apr. 28, 2005

(86) PCT No.: PCT/EP2005/051932

§ 371 (c)(1),
(2), (4) Date: Jun. 18, 2007

(87) PCT Pub. No.: WO2005/105783

PCT Pub. Date: Nov. 10, 2005

(65) Prior Publication Data

US 2007/0293680 A1    Dec. 20, 2007

(30) Foreign Application Priority Data

May 3, 2004    (EP)    .................... 04076321

(51) Int. Cl.
*C07D 215/12*    (2006.01)
*C07D 215/00*    (2006.01)
(52) U.S. Cl. ...................... 546/168; 546/157
(58) Field of Classification Search ............... 546/168, 546/157
See application file for complete search history.

(56) References Cited

U.S. PATENT DOCUMENTS

2007/0293679 A1 * 12/2007 Filliers et al. ............ 546/157

FOREIGN PATENT DOCUMENTS

| WO | WO 97/21701 A | 6/1997 |
|---|---|---|
| WO | WO 01/51127 A | 7/2001 |
| WO | WO 01/53289 A | 7/2001 |
| WO | WO 02/20015 A | 3/2002 |
| WO | WO 02/072574 A | 9/2002 |
| WO | WO 02/079147 A | 10/2002 |

OTHER PUBLICATIONS

International Search Report PCT/EP2005/051932 dated Aug. 5, 2005.
Shaw A.W. et al 'Asymmetric Synthesis of alpha, alpha-diaryl and alpha-aryl-alpha-hetroaryl alkylamines by organometallic additions to N-tert-butanesulfinyl ketimines' Tetrahedron Letters, vol. 42, No. 41, (2001) pp. 7173-7176.

* cited by examiner

*Primary Examiner*—D. Margaret Seaman
*Assistant Examiner*—Nizal S Chandrakumar

(57) ABSTRACT

A diastereoselective synthesis process for the preparation of (R)-(+)-6-[amino(4chlorophenyl)(1-methyl-1H-imidazol-5-yl) methyl]-4-(3-chlorophenyl)-1-methyl2(1H)-quinolinone which comprises the preparation of a compound of formula (XVII): and the stereochemically isomeric forms thereof wherein R is C1-6alkyl or C1-6alkylphenyl.

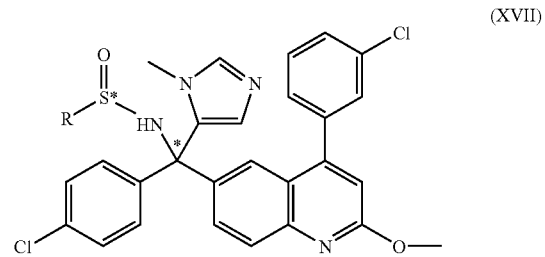

(XVII)

10 Claims, No Drawings

DIASTEREOSELECTIVE SYNTHESIS PROCESS WITH 6-BROMO-4-(3-CHLOROPHENYL)-2-METHOXY-QUINOLINE

CROSS REFERENCE TO RELATED APPLICATIONS

This application is the national stage of Application No. PCT/EP2005/051932, filed Apr. 28, 2005, which claims priority from EPO Patent Application No. 04076321.1, filed May 03, 2004, the entire disclosures of which are hereby incorporated in their entirely.

The present invention relates to the diastereoselective synthesis process of 5-substituted imidazole compounds which have farnesyl tranferase inhibitory activity and to compounds used in the synthesis process for said imidazole compounds.

Farnesyltransferase inhibitors block the main post-translational modification of the Ras protein, thus interfering with its localization to the inner surface of the plasma membrane and subsequent activation of the downstream effectors. Although initially developed as a strategy to target Ras in cancer, farnesyltransferase inhibitors have subsequently been acknowledged as acting by additional and more complex mechanisms that may extend beyond Ras involving GTP-binding proteins, kinases, centromere-binding proteins and probably other farnesylated proteins.

A particular farnesyltransferase inhibitor is described in WO 97/21701, namely (R)-(+)-6-[amino(4-chlorophenyl)(1-methyl-1H-imidazol-5-yl)methyl]-4-(3-chlorophenyl)-1-methyl-2(1H)-quinolinone. The absolute stereochemical configuration of the compound was not determined in the experiments described in the above-mentioned patent specification, but the compound was identified by the prefix "(B)" to indicate that it was the second compound isolated from column chromatography. The compound thus obtained has been found to have the (R)-(+)-configuration. This compound will be referred to below by its published code number R115777 and has the following formula (V).

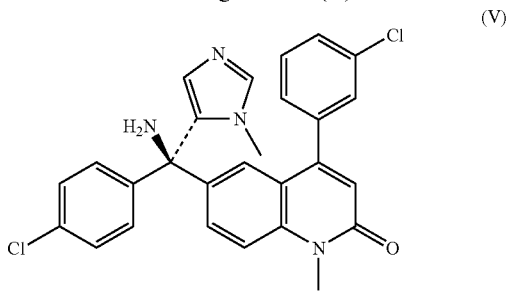

(V)

R115777 (Tipifarnib) is a potent, orally active inhibitor of farnesylprotein transferase. It is one of the most advanced of the farnesylprotein transferase inhibitors currently reported to be in clinical development, being one of the agents that have progressed to phase III studies.

R115777 has been found to have very potent activity against neoplastic diseases. Antineoplastic activity in solid tumors, such as breast cancer, as well as in haematological malignancies, such as leukemia, have been observed. Also combination studies have been carried out demonstrating that R115777 can be safely combined with several highly active anticancer drugs.

In WO 01/53289, the racemates (±) (4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one (racemate 1) and (±) 4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one (racemate 2) are prepared.

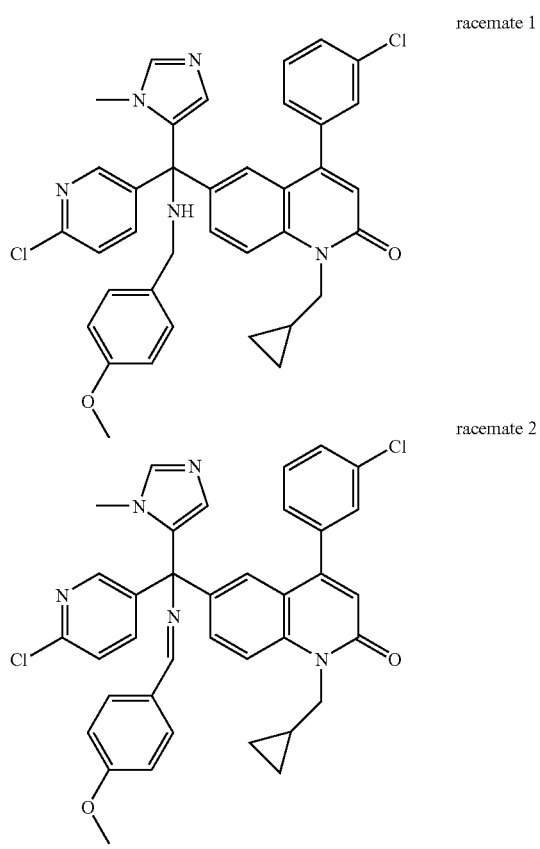

After chiral molecule separation using column chromatography, either the benzylamino or the benzilidine moiety of the resulting (+) and/or (−) enantiomers are converted to an amino group under acidic conditions.

In WO 97/21701, it is described (on page 9, line 7-14) that intermediates of formula (XIII), can be prepared by reacting an intermediate of formula (XIV), wherein W is an appropriate leaving group, such as, for example, halo, with an intermediate ketone of formula (XV). In WO 97/21701, it is described that this reaction can be performed by converting the intermediate of formula (XV) into an organometallic compound, by stirring it with a strong base such as butyl lithium and subsequently adding the intermediate ketone of formula (XV). It is further indicated that although this reaction gives at first instance a hydroxy derivative (i.e. $R^8$ is hydroxy), said hydroxy derivative can be converted into other intermediates wherein $R^8$ has another definition by performing art-known (functional group) transformations. The drawings of the compounds of formula (XIII), (XV) and (XIV) have been taken over from WO 97/21701 and the substituents in these drawings are as defined in WO 97/21701.

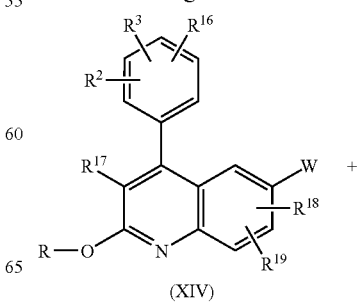

(XIV)

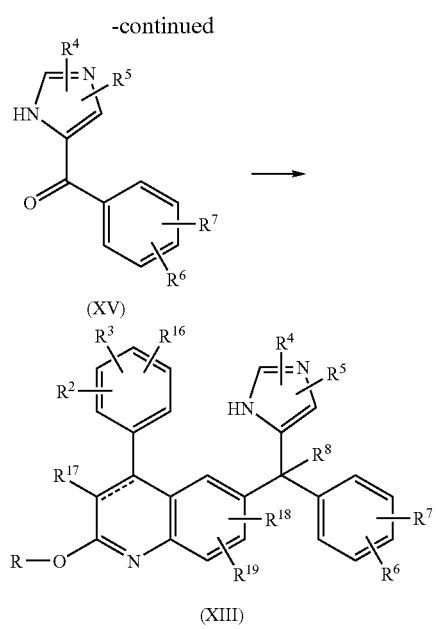

In WO 97/21701, it is also described (from page 7 line 32, to page 8 line 6) that the compounds of formula (XVI), wherein R is $C_{1-6}$alkyl, $R^{(2-8, 16-19)}$ can be a substituent chosen from lists as defined in WO 97/21701 and $R^1$ has a meaning as defined in WO 97/21701 apart from hydrogen, may be prepared by hydrolysing an intermediate ether of formula (XIII), according to art-known methods, such as stirring the intermediate of formula (XIII) in an aqueous acid solution. An appropriate acid can be for instance hydrochloric acid. Subsequently the resulting quinolinone, wherein $R^1$ is hydrogen, may be transformed into a quinolinone of formula (XVI) by art-known N-alkylation. The drawings of the compounds of formula (XIII) and (XVI) have been taken over from WO 97/21701 and the substituents in these drawings are as defined in WO 97/21701.

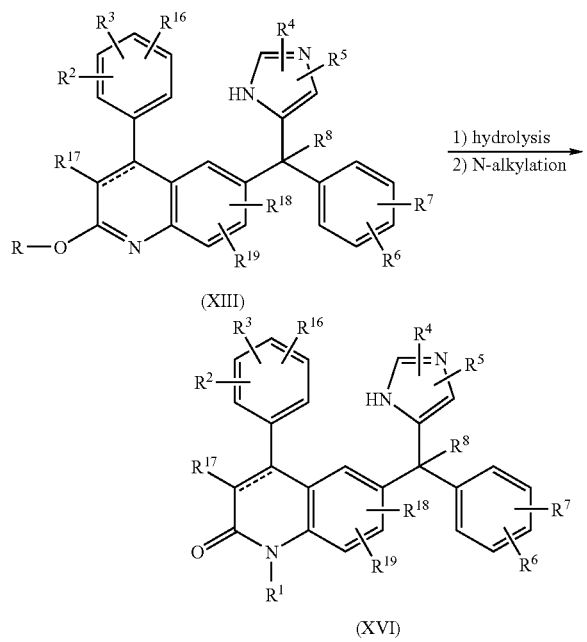

The synthesis of R115777 as originally described in WO 97/21701, is presented in scheme 1.

Herein, in step 1, the intermediate 1-methyl imidazole in tetrahydrofuran, is mixed with a solution of n-butyllithium in a hexane solvent to which is added chlorotriethylsilane (triethylsilyl chloride), followed by a further addition of n-butyllithium in hexane, the resulting mixture being cooled to −78° C. before the addition of a solution of a compound of formula (I), i.e. 6-(4-chlorobenzoyl)-4-(3-chlorophenyl)-1-methyl-2(1H)-quinolinone in tetrahydrofuran. The reaction mixture is subsequently brought to room temperature, and then hydrolysed, extracted with ethyl acetate and the organic layer worked up to obtain a compound of formula (II), i.e. (±)-6-[hydroxy(4-chlorophenyl)(1-methyl-1H-imidazol-5-yl)methyl]-4-(3-chlorophenyl)-1-methyl-2(1H)-quinolinone.

In step 2, the hydroxy compound of formula (II) is chlorinated with thionylchloride to form a compound of formula (III), i.e. (±)-6-[chloro(4-chlorophenyl)(1-methyl-1H-imidazol-5-yl)methyl]-4-(3-chlorophenyl)-1-methyl-2(1H)-quinolinone.

In step 3, the chloro compound of formula (III) is treated, with $NH_4OH$ in tetrahydrofuran to form the amino compound of formula (IV), i.e. (±)-6-[amino(4-chlorophenyl)(1-methyl-1H-imidazol-5-yl)methyl]-4-(3-chlorophenyl)-1-methyl-2(1H)-quinolinone.

In step 4, the amino compound of formula (IV) is separated into its enantiomers by chiral column chromatography over Chiracel OD (25 cm; eluent: 100% ethanol; flow: 0.5 ml/min; wavelength: 220 nm). The pure (B)-fractions are collected and recrystallised from 2-propanol resulting in R115777, the compound of formula (V).

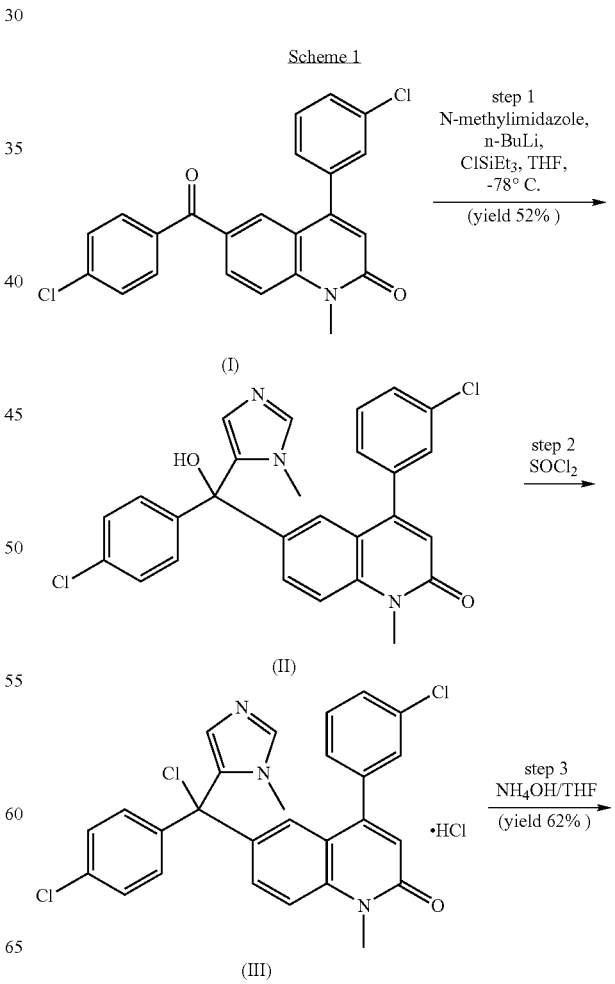

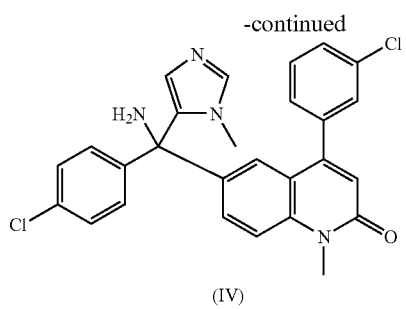

(IV)

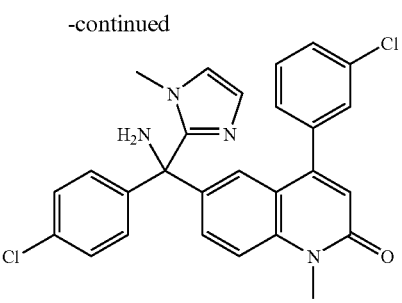

(XII)

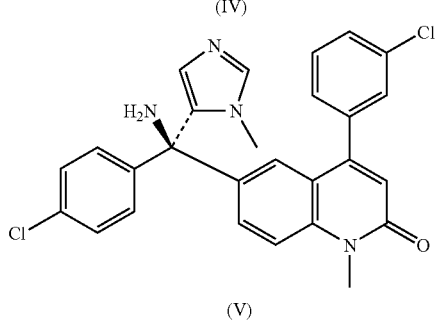

(V)

However, the procedure described in WO97/21701 has a number of disadvantages. For example, during the first step, the procedure results in the undesired formation of a corresponding compound of formula (XI), i.e. 6-[hydroxy(4-chlorophenyl)(1-methyl-1H-imidazol-2-yl)methyl]-4-(3-chlorophenyl)-1-methyl-2(1H)-quinolinone), in which the imidazole ring is attached to the remainder of the molecule at the 2-position of the ring, instead of the desired 5-position. At the end of the procedure, this results in the formation of a compound of formula (XII), i.e. 6-[amino(4-chlorophenyl)(1-methyl-1H-imidazol-2-yl)methyl]-4-(3-chlorophenyl)-1-methyl-2(1H)-quinolinone.

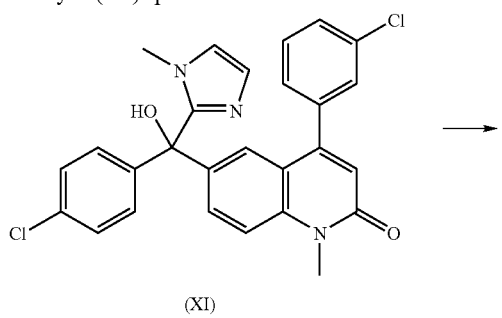

(XI)

Furthermore, the purification of compound (V) using chiral chromatography is expensive and disadvantageous in view of the large amounts of solvent needed and the specialised equipment required to perform a large scale chiral chromatography.

Another process for the synthesis of R115777 as described in WO 02/072574, is presented in scheme 2.

Herein, in step 1, 1-methyl imidazole in tetrahydrofuran is mixed with a solution of n-hexyllithium in a hexane solvent to which is added tri-iso-butylsilyl chloride, followed by a further addition of n-hexyllithium in hexane. The compound of formula (I) in tetrahydrofuran is then added to the reaction mixture, keeping the temperature between −5° C. and 0° C. The resulting product of formula (II) is isolated by salt formation.

In step 2, the chlorination reaction is effected by treatment of the compound of formula (II) with thionyl chloride in 1,3-dimethyl-2-imidazolidinone.

In step 3, the chloro compound of formula (III) is treated with a solution of ammonia in methanol. After the addition of water, the compound of formula (IV), precipitates and can be isolated.

In step 4, the compound of formula (IV) can be reacted with L-(−)-dibenzoyl tartaric acid (DBTA) to form the diastereomeric tartrate salt with formula (VI) i.e. R-(−)-6-[amino(4-chlorophenyl)(1-methyl-1H-imidazol-5-yl)methyl]-4-(3-chlorophenyl)-1-methyl-2(1H)-quinolinone [R—(R*,R*)]-2,3-bis(benzoyloxy)butanedioate (2:3).

Finally, in step 5, the compound of formula (VI) is treated with aqueous ammonium hydroxide, to form the crude compound of formula (V) which is then purified by recrystallisation from ethanol to the pure compound (V).

Scheme 2

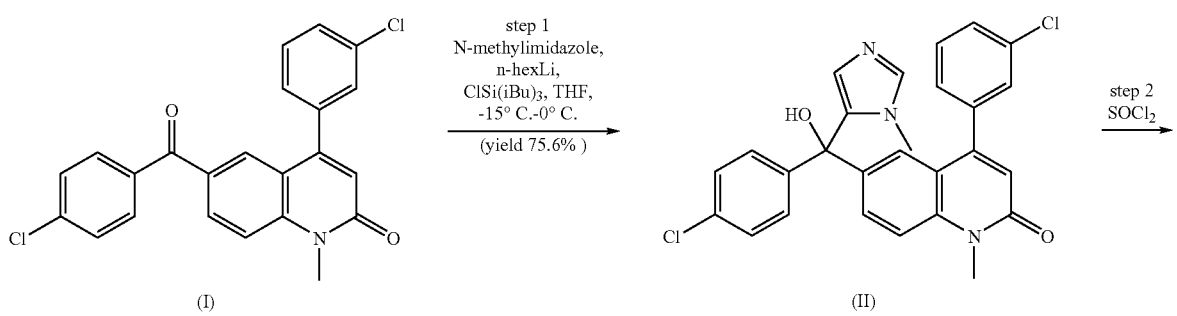

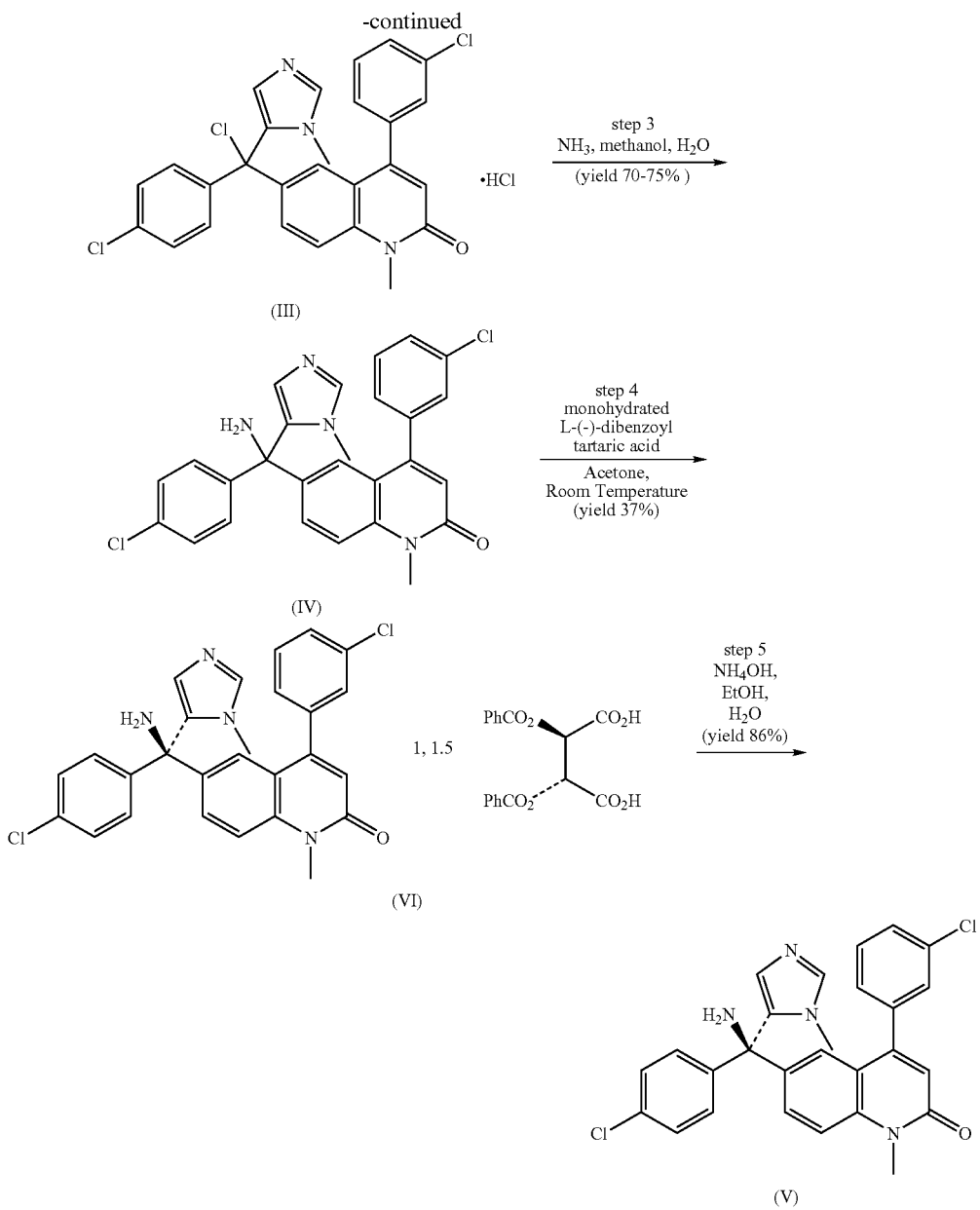

However, in view of the fact that water is present during the third and the fifth step of this procedure, there is significant formation of the hydroxy compound of formula (II). This is important because the compounds of formula (II) and (V) are difficult to separate. In order to keep the quality of the final product (V) as high as possible, it is critical to limit the formation of compound (II).

The major drawback of the above described processes is the generation of large amounts of the other enantiomer that subsequently must be recycled.

Attempts were made to develop processes that solve this problem. One of the possibilities was to enter chirality in the first step of the procedure. A first study was carried out in order to determine if the conversion of an enantiomer of the hydroxy compound of formula (II) into a compound of formula (IV) could preserve chirality.

Several experimental conditions have been tested starting with an enantiomer of a compound of formula (II), but racemisation always occurred.

Shaw et al. (Tetrahedron Letters: 42, 7173-7176) already in 2001, disclosed an asymmetric synthesis process for the production of α-aryl-α-heteroaryl alkylamines using organometallic additions to N-tert-butanesulfinyl ketimines. However, the configuration and the yield of the final enantiomer formed with this process, was depending on the configuration of the N-tert-butanesulfinyl moiety of the ketimines, the composition of the aryl and/or the heteroaryl moieties of the ketimines, as well as on the organo- and the metallic moiety of the organometallic reagent. Furthermore, the use of heteroaryllithium reagents were described in this document, as being in particular disadvantageous, in view of their instability.

Nevertheless, it was tried to put together an N—$C_{1-6}$-alkyl-(S*)-sulfinylketimine containing one part of the molecule of a compound of formula (VI) with an heteroaryllithium compound containing the rest of the molecule in such a way that the resulting N—$C_{1-6}$alkyl-(S*)-sulfinylamine could be used for conversion into a compound of formula (IV).

One approach was to diverge from the classical synthesis scheme of R115777 and try to enter the 4-phenylquinolinone backbone onto a N—$C_{1-6}$alkyl-(S*)-sulfinylketimine prepared from (4-chlorophenyl)(1-methyl-1H-imidazol-5-yl)methanone. Trial and error learned that the 4-phenylquinolinone backbone can not be directly introduced, that it is preferable to perform a bromine-lithium exchange on a 6-bromo-4-(3-chlorophenyl)-2-methoxy-quinoline and that in contrast to the procedure described by Shaw et al., the N—$C_{1-6}$alkyl-(S*)-sulfinylketimine prepared from (4-chlorophenyl)(1-methyl-1H-imidazol-5-yl)methanone should be added to the organolithium compound and not vice versa.

Thus the present invention solves the above described problems. It provides a new process for the preparation of a compound of formula (IV), without the need to recycle one of the enantiomers, while minimising the formation of undesired isomers and impurities and under conditions which offer economic advantages for operation on a commercial scale.

The present invention provides a process for the preparation of a compound of formula (XVII)

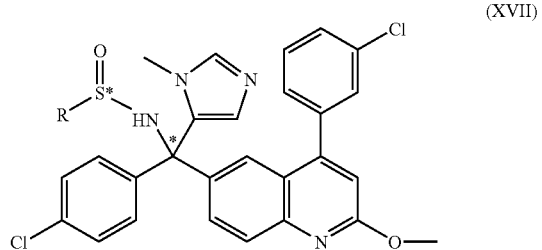

(XVII)

wherein R is $C_{1-6}$alkyl or $C_{1-6}$alkylphenyl- which comprises reacting a compound of formula (XVIII)

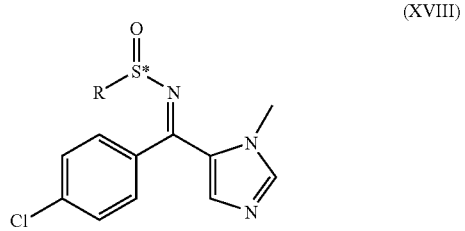

(XVIII)

wherein R is $C_{1-6}$alkyl or $C_{1-6}$alkylphenyl-, with 6-bromo-4-(3-chlorophenyl)-2-methoxy-quinoline.

As used in the foregoing definitions and hereinafter $C_{1-6}$alkyl defines straight and branched chain saturated hydrocarbon radicals having from 1 to 6 carbon atoms such as, e.g. methyl, ethyl, propyl, butyl, 1-methylethyl, 2-methylpropyl, pentyl, 2-methyl-butyl, hexyl, 2-methylpentyl and the like.

(S(R)) in the chemical name of some compounds means that the sulfur-atom in the molecule is in the R-configuration and (S(S)) means that the sulfur-atom in the molecule is in the S-configuration.

In the above described process, the diastereomeric excess of a compound of formula (XVII) is generally higher than 80%, most preferably higher than 94%. The two diastereomers can be further purified (from the other diastereomer) by standard techniques like crystallisation or chromatography.

In more detail, the reaction may be conveniently effected by initially preparing a solution of 6-bromo-4-(3-chlorophenyl)-2-methoxy-quinoline in a solvent such as tetrahydrofuran, to which is added n-butyllithium in a solvent such as n-hexane at a temperature of −78° C. The compound of formula (XVIII) in a solvent such as tetrahydrofuran is then added to the reaction mixture, keeping the temperature at −78° C.

The number of equivalents of 6-bromo-4-(3-chlorophenyl)-2-methoxy-quinoline used during the diastereoselective synthesis process of a compound of formula (IV) is generally one, preferably 1.25 or more.

The number of equivalents of n-butyllithium used during the diastereoselective synthesis process of a compound of formula (IV) is generally 1.1, preferably 1.35 or more.

The number of equivalents of the compound of formula (XVIII) used during the diastereoselective synthesis process of a compound of formula (IV) is generally between 1 and 1.3, preferably lower than the equivalents of 6-bromo-4-(3-chlorophenyl)-2-methoxy-quinoline and n-butyllithium.

The concentration of the compound of formula (XVIII) is generally higher than 0.2 mol/L, preferably higher than 0.55 mol/L, most preferably higher than 1.65 mol/L.

Another feature of the present invention are the compounds of formula (XVIII)

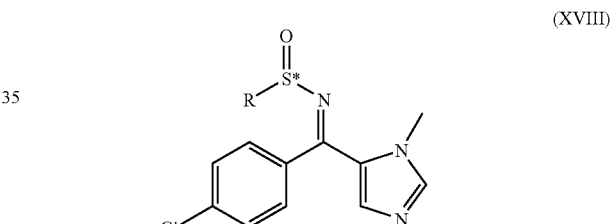

(XVIII)

and the stereochemically isomeric forms thereof wherein R is $C_{1-6}$alkyl or $C_{1-6}$alkylphenyl-.

Compounds of formula (XVIII) can be present as E and Z isomers which can rapidly interconvert.

Preferred compounds of formula (XVIII), are those compounds of formula (XVIII) wherein R is methylpropyl or methylphenyl, more preferably 2-methyl-2-propanyl or 4-methylphenyl. Most preferred compounds of formula (IX) are compound 22, i.e. N-[(4-chlorophenyl)(1-methyl-1H-imidazol-5-yl)methylene)]-2-methyl-2-propanesulfinamide, compound 23, i.e. N-[(4-chlorophenyl)(-1-methyl-1H-imidazol-5-yl)methylene]-p-toluenesulfinamide, compound 25, and compound 29.

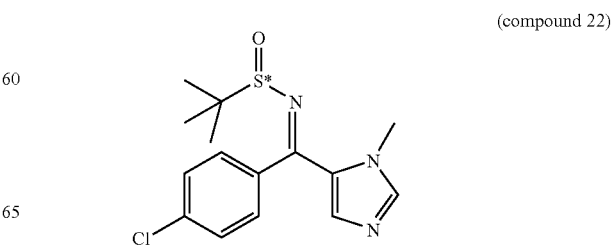

(compound 22)

-continued

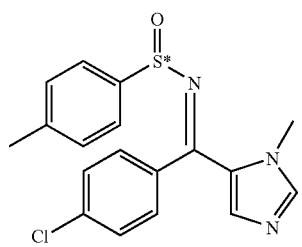
(compound 23)

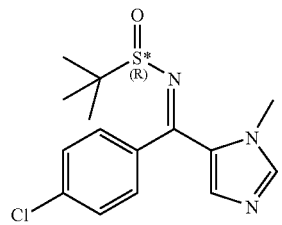
(compound 25)

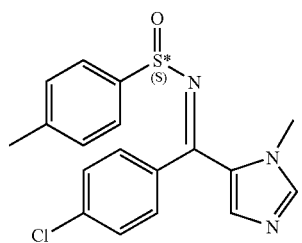
(compound 29)

The compound of formula (XVIII) wherein R is $C_{1-6}$alkyl or $C_{1-6}$alkylphenyl-, can be made by addition of a chiral sulfinamide of formula (X), wherein R is $C_{1-6}$alkyl or $C_{1-6}$alkylphenyl-, in the presence of titanium (IV) ethoxide and a suitable solvent, such as dichloromethane, preferably dichloroethane or tetrahydrofuran.

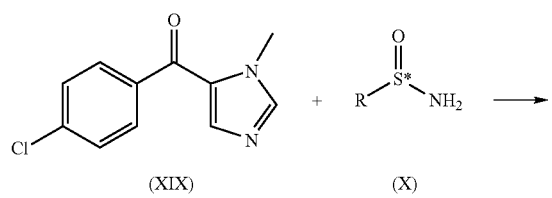

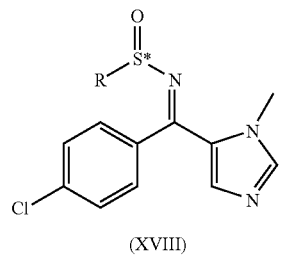
(XVIII)

R in the chiral sulfinamide of formula (X) is preferable 2-methyl-2-propanyl or 4-methylphenyl.

The term chiral sulfinamide of formula (X) means the compound of formula (X), wherein the enantiomeric excess is 40% or higher, preferably higher than 60%, more preferably higher than 80%, most preferably higher than 94%.

Another feature of the present invention is a compound of formula (XVII)

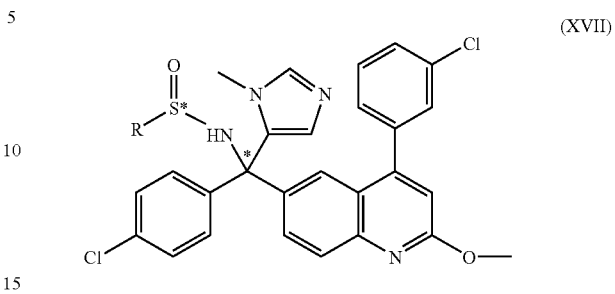
(XVII)

and the stereochemically isomeric forms thereof wherein R is $C_{1-6}$alkyl or $C_{1-6}$alkylphenyl-.

Preferred compounds of formula (XVII) are those compounds wherein R is 2-methyl-2-propyl. More preferred compound of formula (XVII) are compound 24, i.e. N-[(4-chlorophenyl)((4-(3-chlorophenyl)-2-methoxy-quinoline-6-yl)(1-methyl-1H-imidazole-5-yl)methyl]-2-methyl-2-propanesulfinamide and compound 26.

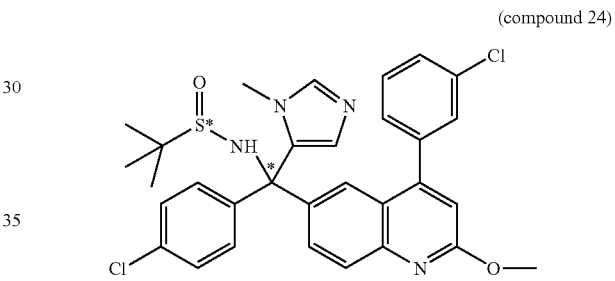
(compound 24)

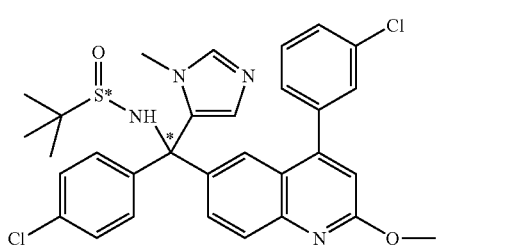
(compound 26)

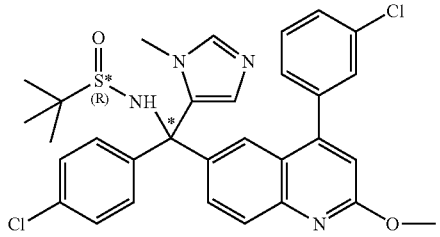

A compound of formula (XVIII) can be converted into a compound of formula (XX) under acidic conditions, for example by addition of hydrochloric acid, in a suitable solvent, for example isopropanol or methanol, at a suitable temperature, for example room temperature.

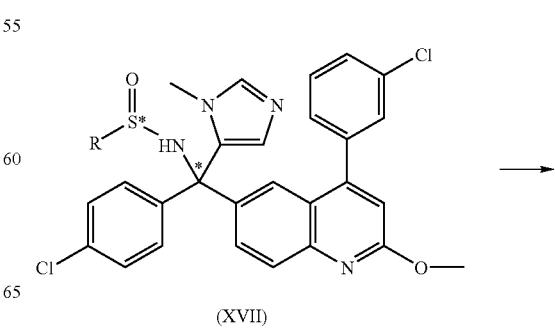
(XVII)

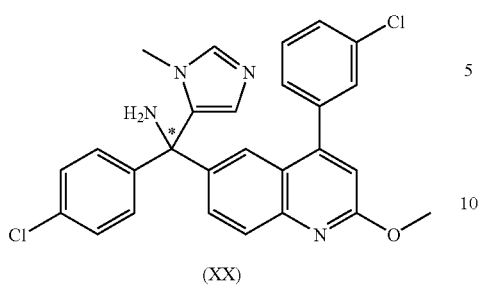

(XX)

The quinolonone of formula (XXI) can be prepared by hydrolysing the compound of formula (XX) with an appropriate acid, such as hydrochloric acid, in a suitable solvent, such as tetrahydrofuran.

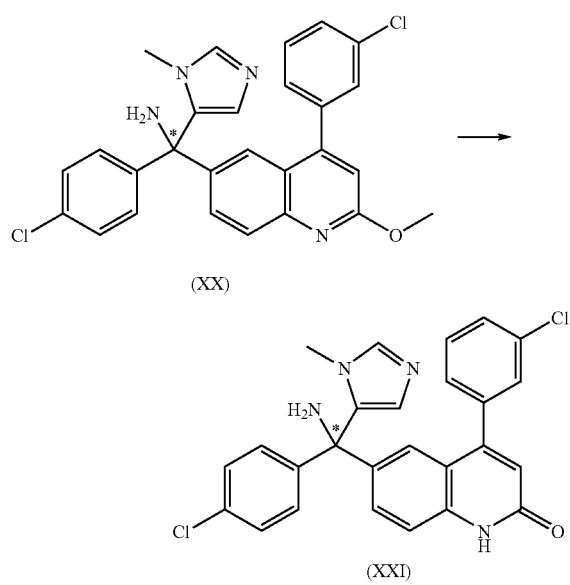

(XX)

(XXI)

The quinolinone of formula (IV) can be prepared by N-alkylation of the compound of formula (XXI) with an appropriate alkylating agent, such as methyliodide, in a suitable solvent, such as tetrahydrofuran, in the presence of a suitable base, such as sodium hydroxide and a suitable phase transfer agent, such as benzyltriethylammonium chloride.

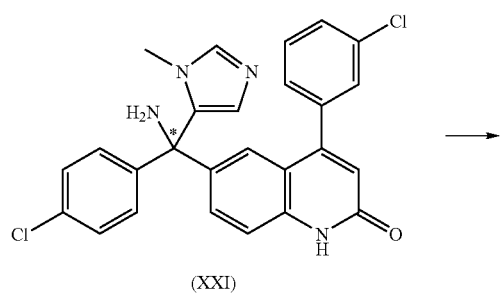

(XXI)

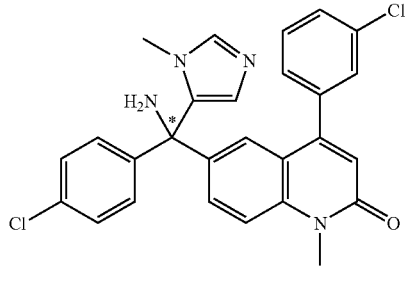

(IV)

After conversion of a compound of formula (XVII) into the enantiomers of formula (XX), (XXI) and (IV), racemisation does not appear. Thus in the above described process, the enantiomeric excess of a compound of formula (XX), (XXI) and (IV) is generally higher than 80%, most preferably higher than 94%. The enantiomers of formula (XX), (XXI) and (IV) can be further purified (from the other enantiomer) by standard techniques, such as crystallisation.

The pharmaceutically acceptable acid addition salts as mentioned hereinabove are meant to comprise the therapeutically active non-toxic acid and non-toxic base addition salt forms which the compounds of formula (XVII) and (XVIII) are able to form. The compounds of formula (XVII) and (XVIII) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The terms acid addition salt also comprise the hydrates and the solvent addition forms which the compounds of formula (XVII) and (XVIII) are able to form. Examples of such forms are e.g. hydrates, alcoholates and the like.

The term stereochemically isomeric forms of compounds of formula (XVII) and (XVIII), as used hereinbefore, defines all possible compounds made up of the same atoms bonded by the same sequence of bonds but having different three-dimensional structures which are not interchangeable, which the compounds of formula (XVII) and (XVIII) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (XVII) and (XVIII) both in pure form or in admixture with each other are intended to be embraced within the scope of the present invention.

The following examples illustrate the present invention.

Hereinafter "BTEAC" means benzyltriethylammonium chloride, "DCM" means dichloromethane, "DCE" means dichloroethane "EtOAc" means ethyl acetate, "MeOH" means methanol, "Ti(OEt)$_4$" means titanium (IV) ethoxide, and "THF" means tetrahydrofuran.

A. Preparation of Intermediates

EXAMPLE A.1 a) Preparation of N-[(4-chlorophenyl)(1-methyl-1H-imidazol-5-yl)methylene)]-2-methyl-2-propanesulfinamide [(S(R)] (Compound 25)

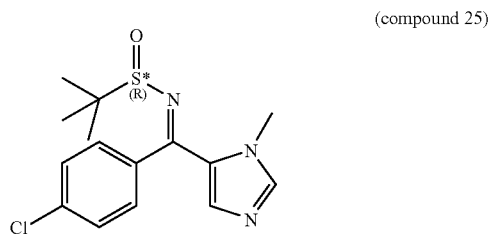
(compound 25)

Ti(OEt)$_4$ (0.0162 mol) was added to a mixture of (4-chlorophenyl)(1-methyl-1H-imidazol-5-yl)methanone (0.0032 mol) and (R)-(+)-2-methyl-2-propane-sulfinamide (0.0032 mol) in DCE (7 ml). The mixture was stirred and refluxed for 6 days, then cooled to room temperature. Ice water was added. The mixture was filtered over celite. Celite was washed with DCM. The organic layer was extracted with saturated sodium chloride. The organic layer was separated, dried (MgSO$_4$), filtered, and the solvent was evaporated. This fraction was purified by column chromatography over silica gel (40 μm) (eluent: DCM/MeOH/NH$_4$OH 97/3/0.5), yielding 0.475 g of compound 25 (46%).

The compound N-[(4-chlorophenyl)(1-methyl-1H-imidazol-5-yl)methylene)]-2-methyl-2-propanesulfinamide [(S(S)] can be obtained in an analogous way.

b) Preparation of N-[(4-chlorophenyl)((4-(3-chlorophenyl)-2-methoxy-quinoline-6-yl)(1-methyl-1H-imidazole-5-yl)methyl]-2-methyl-2-propanesulfinamide [S(R)] (Compound 26)

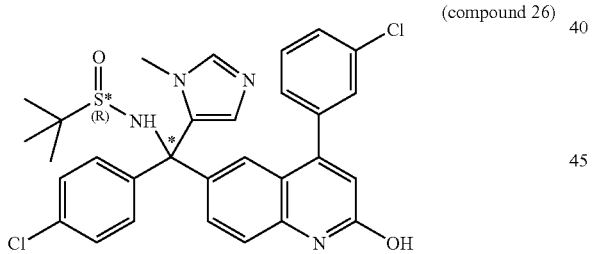
(compound 26)

n-Butyllithium (0.00081 mol) in hexane, was added dropwise at −78° C. to a mixture of 6-bromo-4-(3-chlorophenyl)-2-methoxy-quinoline (0.00081 mol) in THF (3 ml) under nitrogen flow. The mixture was stirred at −78° C. for 30 minutes. A solution of compound 25 (0.00065 mol) in THF (0.6 ml) was added. The mixture was stirred at −78° C. for 1 hour and 30 minutes, poured out into ice water and extracted with EtOAc. The organic layer was separated, dried (MgSO4), filtered, and the solvent was evaporated. This fraction was purified by column chromatography over silica gel (40 μm)(eluent: DCM/MeOH/NH$_4$OH 97/3/0.1). The pure fractions were collected and the solvent was evaporated, yielding 0.138 g (36%) of compound 26, melting point 153° C.

The compound N-[(4-chlorophenyl)((4-(3-chlorophenyl)-2-methoxy-quinoline-6-yl)(1-methyl-1H-imidazol-5-yl)methyl]-2-methyl-2-propanesulfinamide [S(S)] can be obtained in an analogous way c) Preparation of (S)-1-(4-chlorophenyl)-1-[4-(3-chlorophenyl)-2-methoxy-quinoline-6-yl]-1-(1-methyl-1H-imidazole-5-yl)-methylamine (Compound 27)

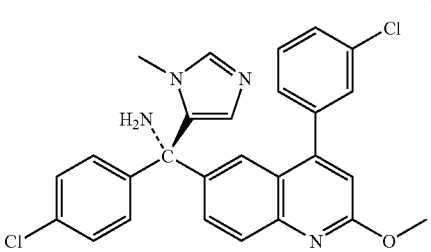
(compound 27)

Hydrochloric acid in isopropanol was added to a solution of compound 26 (0.000018 mol) in methanol (4.2 ml). The mixture was stirred at room temperature for 30 minutes. The mixture was added to potassium carbonate (10%) on ice and extracted with ethyl acetate. The organic layer was separated, washed with a solution of saturated sodium chloride, dried (MgSO$_4$), filtered, and evaporated giving 0.086 g (100%) of compound 27, melting point 96° C., enantiomeric excess 88%.

d) Preparation of (S)-6-[amino(4-chlorophenyl)(1-methyl-1H-imidazol-5-yl)methyl]-4-(3-chlorophenyl)-1H)-quinolin-2-one (Compound 28)

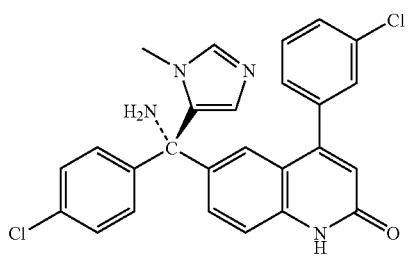
(compound 28)

Compound 27 (0.00038 mol) in hydrochloric acid 3N (9.25 ml) and THF (9.25 ml), was stirred at 60° C. for 24 hours and evaporated, giving 0.18 g (100%) of compound 28, melting point 210° C.

EXAMPLE A.2 a) Preparation of N-[(4-chlorophenyl)(1-methyl-1H-imidazol-5-yl)methylene)]-p-toluenesulfinamide [(S(S)](Compound 29)

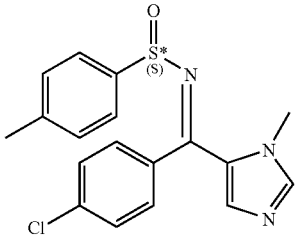
(compound 29)

Ti(OEt)$_4$ (0.0419 mol) was added to a mixture of (4-chlorophenyl)(1-methyl-1H-imidazol-5-yl)methanone (0.0084 mol) and (S)-(+)-p-toluenesulfinamide (0.0084 mol) in DCE (18 ml). The mixture was stirred and refluxed for 7 days, then cooled to room temperature. Ice water was added. The mixture was filtered over celite. Celite was washed with DCM. The organic layer was extracted with saturated sodium chloride. The organic layer was separated, dried (MgSO4), filtered, and the solvent was evaporated. This fraction was purified by column chromatography over silica gel (40 µm) (eluent: DCM/MeOH/NH₄OH 97/3/0.5), yielding 1.15 g of compound 29 (38%).

The compound N-[(4-chlorophenyl)(1-methyl-1H-imidazol-5-yl)methylene)]-p-toluenesulfinamide [(S(R)] can be obtained in an analogues way.

B. Preparation of Final Compounds

EXAMPLE B.1 a) Preparation of (S)-6-[amino(4-chlorophenyl)(1-methyl-1H-imidazol-5-yl)methyl]-4-(3-chlorophenyl)-1-methyl-2(1H)-quinolinone (Compound 30)

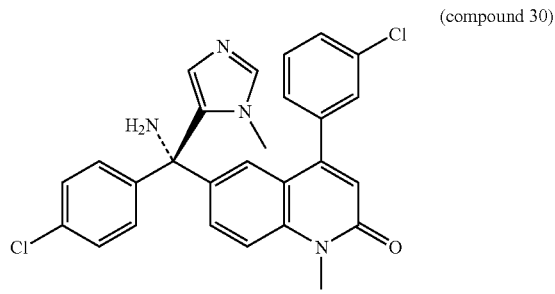
(compound 30)

Compound 28 (0.00038 mol) was added to a solution of THF (1.8 ml) and NaOH 10N (1.8 ml). BTEAC (0.0019 mol) and methyliodide (0.00076 mol) were added and the mixture was stirred for 2 hours at room temperature. EtOAc was added. The organic layer was separated, dried (MgSO₄), filtered, and evaporated giving 0.149 g (83%) of compound 30, enantiomeric excess 86%.

The invention claimed is:

1. A process for the preparation of a compound of formula (XVII)

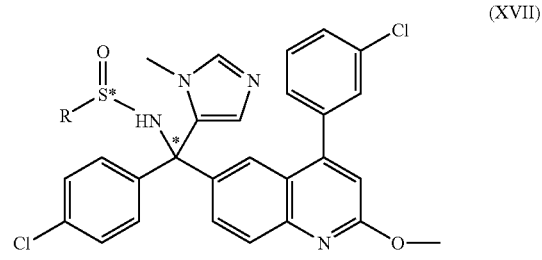
(XVII)

wherein R is $C_{1-6}$alkyl or $C_{1-6}$alkylphenyl, said process comprising reacting a compound of formula (XVIII)

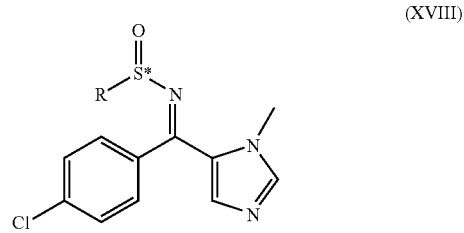
(XVIII)

wherein R is $C_{1-6}$alkyl or $C_{1-6}$alkylphenyl, with 6-bromo-4-(3-chlorophenyl)-2-methoxy-quinoline.

2. A process as claimed in claim 1 wherein the diastereomeric excess of a compound of formula (XVII) is 80% or higher.

3. A process as claimed in claim 1 wherein
a) n-butyllithium is added to a solution of 6-bromo-4-(3-chlorophenyl)-2-methoxy-quinoline in tetrahydrofuran,
b) the compound of formula (XVIII) is added to the reaction mixture, and
c) the temperature is kept at −78° C.

4. A process as claimed in claim 3 wherein
d) the number of equivalents of 6-bromo-4-(3-chlorophenyl)-2-methoxy-quinoline is 1.25 or more,
e) the number of equivalents of n-butyllithium is 1.35 or more,
f) the number of equivalents of the compound of formula (XVIII) is 1, and
g) the concentration of the compound of formula (XVIII) is higher than 0.55 mol/L.

5. A process as claimed in claim 1 wherein
h) the compound of formula (XVIII) is prepared by addition of a chiral sulfinamide of formula (X) to the compound of formula (XIX),

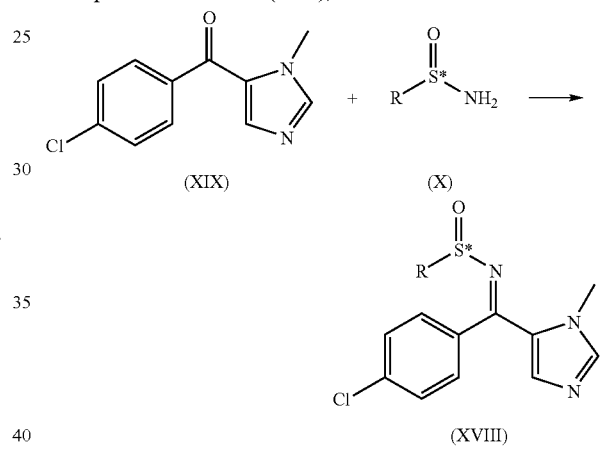

i) the compound of formula (XVII) is converted into the compound of formula (XX) under acidic conditions, in a suitable solvent, at a suitable temperature,

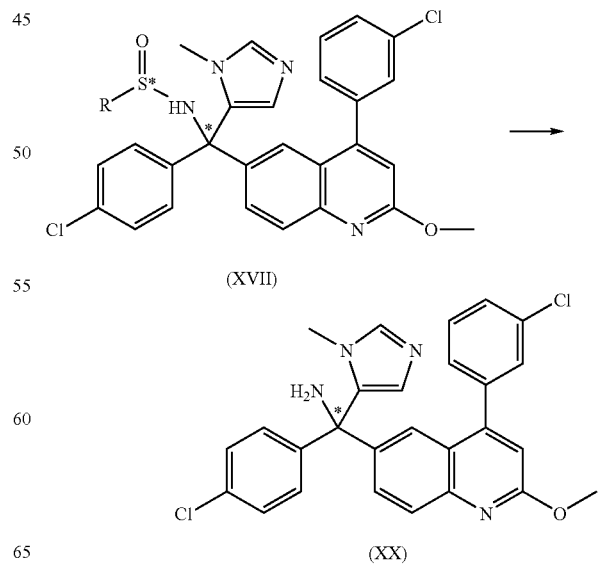

j) the compound of formula (XXI) is prepared by hydrolysing the compound of formula (XX) with an appropriate acid in a suitable solvent, and

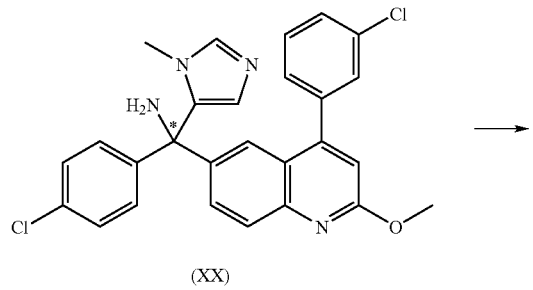

(XX)

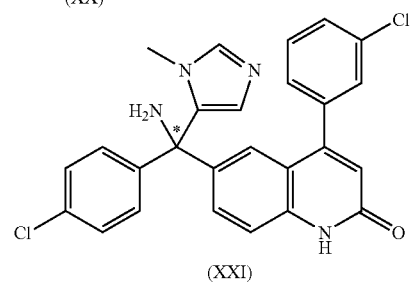

(XXI)

k) the quinolinone of formula (IV) is prepared by N-alkylation the compound of formula (XXI) with an appropriate alkylating agent, in a suitable solvent.

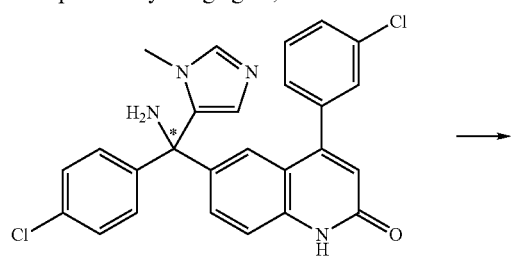

(XXI)

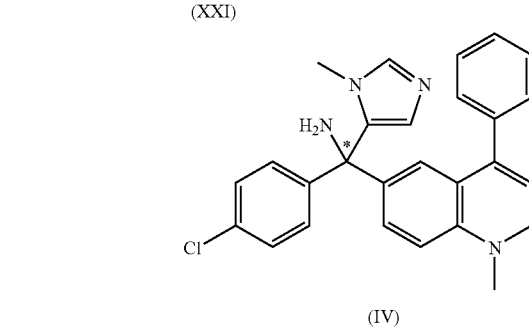

(IV)

6. A process as claimed in claim 5 wherein the chiral sulfinamide of formula (X) is 2-methyl-2-propane-sulfinamide or p-toluenesulfinamide.

7. A compound of formula (XVIII)

(XVIII)

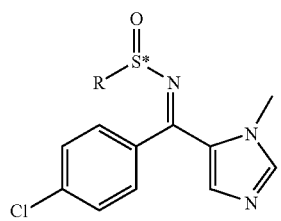

and the stereochemically isomeric forms thereof wherein R is $C_{1-6}$alkyl or $C_{1-6}$alkylphenyl-.

8. A compound selected from the group consisting of:

(compound 22)

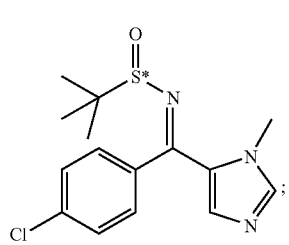

(compound 23)

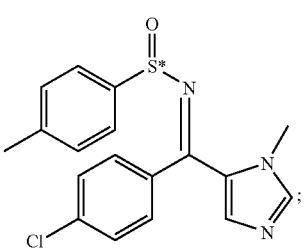

(compound 25)

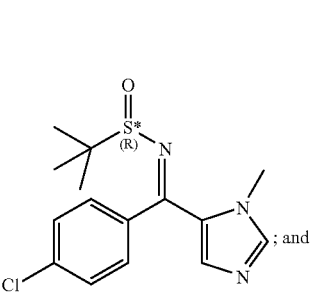

; and (compound 29)

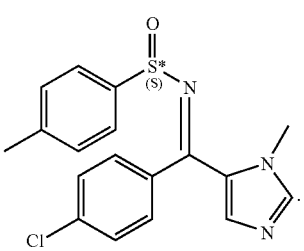

9. A compound of formula (XVII)

(XVII)

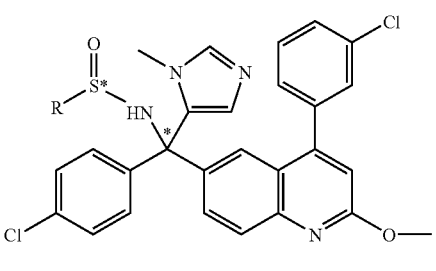

and the stereochemically isomeric forms thereof wherein R is $C_{1-6}$alkyl or $C_{1-6}$alkylphenyl.

10. A compound selected from the group consisting of:
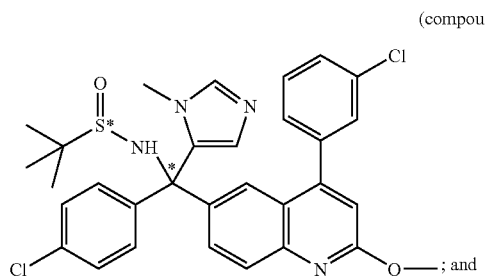
(compound 24)
; and
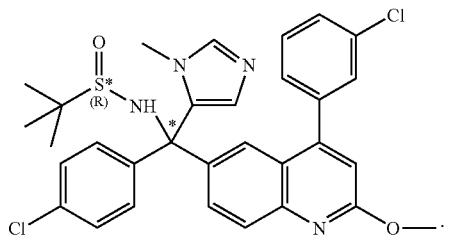
(compound 26)
* * * * *